United States Patent [19]

Khmelevskaya et al.

[11] 4,214,113
[45] Jul. 22, 1980

[54] METHOD FOR CARRYING OUT PYROLYSIS OF HYDROCARBON STARTING PRODUCTS

[76] Inventors: Elena D. Khmelevskaya, Yaroslavskoe shosse, 142, kv. 106, Moscow; Grigory I. Dvoskin, Mytischi, Sharapovsky proezd, 18, kv. 4, Moskovskaya oblast; Vladislav A. Kablikov, Sretensky bulvar, 6/1, kv. 122, Moscow; Zinovy F. Chukhanov, ulitsa D. Ulyanova, 3, kv. 40, Moscow; Vadim M. Volny, ulitsa Butlerova, 34, korpus 1, kv. 29, Moscow; Tamara N. Mukhina, Festivalnaya ulitsa, 15, korpus 3, kv. 44, Moscow; Genrikh L. Stolyar, Kievskaya ulitsa, 18, kv. 51, Moscow; Olga E. Volnaya, ulitsa Butlerova, 34, korpus 1, kv. 29, Moscow; Nikolai F. Kuptsov, ulitsa Shafeeva, 18, kv. 25, Ufa, all of U.S.S.R.

[21] Appl. No.: 966,781

[22] Filed: Dec. 6, 1978

Related U.S. Application Data

[62] Division of Ser. No. 811,137, Jun. 28, 1977.

[51] Int. Cl.$^2$ ............................................. C07C 3/30
[52] U.S. Cl. ..................................... 585/634; 585/648
[58] Field of Search ................... 260/683 R; 208/125; 585/634, 648

[56] References Cited
FOREIGN PATENT DOCUMENTS
487926 10/1975 U.S.S.R. ............................. 260/683 R Primary Examiner—George Crasanakis
Attorney, Agent, or Firm—Steinberg & Blake

[57] ABSTRACT

Pyrolysis of hydrocarbon starting products is carried out in a cylindrical casing containing a liquid heat carrier at a predetermined level in the casing. The casing is split into a heating zone and a pyrolysis zone by a cylindrical baffle which extends a small distance below the surface of the heat carrier. A jet directs a gaseous heating agent onto the surface of the heat carrier in the heating zone. Another jet directs hydrocarbon starting products onto the surface of the heat carrier in the pyrolysis zone where pyrolysis products are formed.

3 Claims, 7 Drawing Figures

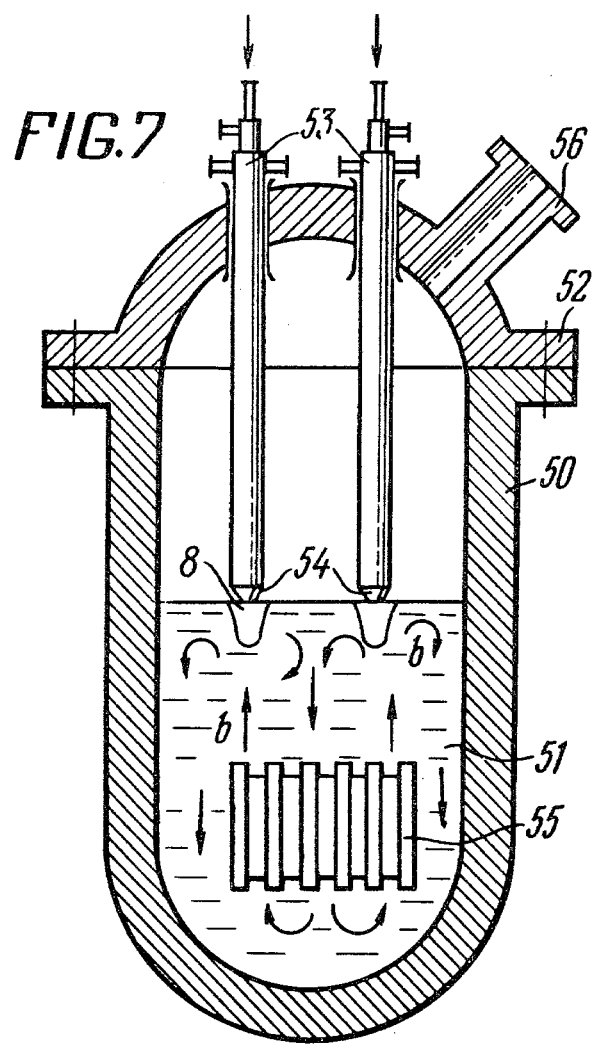

METHOD FOR CARRYING OUT PYROLYSIS OF HYDROCARBON STARTING PRODUCTS

This is a division of application Ser. No. 811,137, filed June 28, 1977.

The invention relates to the equipment for processing hydrocarbon starting products, and more particularly to an apparatus and method for pyrolysis of hydrocarbon starting products.

The invention may be most advantageously used in the processing of various hydrocarbon starting products to obtain valuable chemical products, such as lower olefins and aromatic hydrocarbons.

In addition, the invention may find its application in the construction of heat-exchange apparatus.

Known in the art is an apparatus for pyrolysis of hydrocarbon starting products comprising a horizontally split casing for molten heat carrier. The upper part of the casing is provided with at least one injector having a nozzle for feeding hydrocarbon starting products into the molten heat carrier and with at least one pipe for removing pyrolysis products. The apparatus also comprises means for supplying heat to the heat carrier.

In the prior art apparatus, hydrocarbon starting products are fed into the molten heat carrier below the surface level of the melt. The starting products are fed through the nozzle into the molten heat carrier at a velocity which does not exceed 0.5 m/s. Under the action of high temperature of molten heat carrier, reactions occur in hydrocarbon starting products to result in the formation of molecules with lower molecular weight. Thus, liquid hydrocarbons are converted into gaseous phase so that a large quantity of bubbles are formed in the space around the nozzle which ascend to the surface of the heat carrier at a velocity of about 0.3–0.4 m/s.

The above-described apparatus features a long residence time of starting products in the high-temperature zone and low rate of heating of the products which is very important for the pyrolysis.

Long residence time and low rate of heating of starting products result in reduced yield of valuable chemical products.

The ascent velocity of bubbles restricts the productivity of the apparatus. The diameter of bubbles is also important: the smaller the bubbles, the higher the rate of heating of starting products. The smaller the bubbles, the slower their ascent, that is with smaller bubbles the admissible load on the apparatus de-creases.

Generally, the residence time of starting products in the high-temperature zone during the pyrolysis varies from 0.05 to 0.5 s to ensure sufficiently high yield of valuable chemical products, such as olefins.

With longer residence time of starting products in the high-temperature zone, molecules of olefins have the time to decompose to $H_2$ and C, whereas with shorter residence time, there is no time sufficient for the decomposition reaction to occur.

As mentioned above, the ascent velocity of bubbles varies from 0.3 to 0.4 m/s. In order to provide for the residence time of starting products in the above-mentioned zone of 0.5 s, the nozzle should be submerged at $0.4 \times 0.5 = 0.2$ m. With such submergence of the nozzle, the starting products have no time to be heated to required pyrolysis temperatures from 700° to 950° C., and with greater submergence of the nozzles, the yield of valuable chemical products, such as olefins is lowered.

Long-term residence in the high-temperature zone results in a greater yield of carbon (coke) (up to 30–40%) thus hampering operation of the apparatus because the working space thereof is filled with coke, and the deposition of coke on the heat-exchange surfaces results in lower heat removal rate and deterioration of the surfaces. In order to ensure sufficiently high yield of olefins, it is necessary that the rate of heating of starting products be above $10^5$ C./s. With large-sized bubbles, heat transfer to the inner space of the bubbles is hampered by low heat conductance of gas and insignificant role of convective heat transfer.

For ensuring high heating rate, attempts are made to have bubbles as small as possible; small-diameter bubbles, however, bring about a very low ascent velocity which, as mentioned, results in impaired performance of the pyrolysis.

In order to minimize the influence of the above negative aspects, the process is conducted by feeding starting products through a large number of fine nozzles with a small thickness of heat carrier layer (up to 0.5 m). This, however, results in an increased area of the heat carrier bath and complicated system for distribution of starting products.

The above-described aspects of the pyrolysis in the prior art apparatus do not enable the improvement of its productivity because with an increased starting product feeding rate, the volume of heat carrier is overfilled with gaseous phase, and the resultant scum is ejected from the apparatus leading to its failure.

Where viscous heat carriers are used, the ascent velocity of bubbles is much lower so that the ejection of heat carrier occurs with lower loads of the apparatus.

It is the main object of the invention to provide an apparatus for pyrolysis of hydrocarbon starting products which enables the reduction of residence time of starting products in the heat carrier thereby intensifying the pyrolysis process.

The above and other objects are accomplished in an apparatus for pyrolysis of hydrocarbon starting products comprising a horizontally split casing for molten heat carrier accommodating, in the upper part thereof, at least one injector having a nozzle for feeding hydrocarbon starting products into molten heat carrier and at least one pipe for removing pyrolysis products, and means for supplying heat to the heat carrier, wherein, according to the invention, the injector is arranged in the upper part of the casing in such a manner that the outlet section of the nozzle thereof is spaced apart from the heat carrier surface at a distance sufficient for the formation of a hydrodynamic crater in the heat carrier surface under the action of a jet of hydrocarbon starting products flowing from the nozzle, and means for supplying heat is arranged within the casing in such a manner that heat is supplied directly within the heat carrier.

The above-described arrangement of the injector and nozzle enables the rate of supply of hydrocarbon starting products which is sufficient for the formation of a hydrodynamic crater in the heat carrier with a depth ensuring sufficiently intensive supply of heat to the products subjected to pyrolysis.

The arrangement of means for supplying heat within the casing provides for intensification of heat supply and elimination of overheating of the casing material.

The casing is preferably provided with a baffle having one extremity secured to the upper part of the casing, the other extremity being in a slightly spaced relationship with the outlet section of the nozzle and in such a manner that the space over the heat carrier is divided into at least two zones, the injector with the nozzle for feeding hydrocarbon starting products being arranged in one zone, and means of supplying heat to heat carrier, in the other zone, means for supplying heat comprising at least one injector having a nozzle secured to the upper part of the casing for feeding gaseous heating agent to the surface of heat carrier.

The provision of the baffle which divides the space over the heat carrier into two zones and the construction of means for supplying heat according to the invention ensure heat supply to the heat carrier with the intensity which is equal to the intensity of heat removal. The equality of these intensities enables an improvement of reliability of operation of the apparatus and ensures its operation over a large range of varying performances because the removal of heat does not restrict the load of the apparatus in terms of starting products.

The centers of the outlet sections of the injectors for feeding hydrocarbon starting products and gaseous heating agent are preferably located at the surface of heat carrier.

Due to the above-mentioned arrangement of the centers, maximum intensity of heat transfer in the craters is achieved since in such case, with other conditions of feeding of starting products being equal, the crater depth and flow velocity therein are at the maximum compared to the feeding of starting products through a nozzle located somewhat above the heat carrier surface.

The apparatus according to the invention may have the casing of cylindrical form.

In case the casing is cylindrical, the baffle may be annular so as to ensure minimum resistance offered by the casing and baffle to the circular flow of heat carrier around the central zone of the casing.

The nozzles of the injectors for feeding hydrocarbon starting products and gaseous heating agent are preferably mounted at an acute angle to the surface of heat carrier and at an acute angle to the radius of the cylindrical casing drawn through the center of the outlet section of the injector nozzle.

This arrangement of the injectors with the cylindrical casing and annular baffle provides for the flow of heat carrier in the zone adjacent to the surface thereof in two directions: radial direction, from the center to the periphery, and circular direction about the center of the casing under the action of jets flowing from the injector nozzles. Thus, the overflow of heat carrier from the heating zone to the pyrolysis zone is intensified thus intensifying the heat transfer between these zones.

In order to optimize the heat transfer between the zones, the angle of inclination of the nozzles to the surface of heat carrier is preferably from 10° to 40°, and the angle of inclination of the nozzles to the radius of the casing drawn through the center of the outlet section of the injector nozzles is preferably from 15° to 75°.

For continuous operation of the apparatus with continuous removal of coke formed during the pyrolysis, the casing may be provided with an additional annular baffle arranged between the casing and injectors in such a manner that the upper extremity of the baffle is below the heat carrier surface to enable its overflow, the baffle having perforations in the lower part thereof.

In case the apparatus according to the invention is used for the pyrolysis in heat carriers of elevated viscosity (more than 1 P), the casing is preferably rotatable about the vertical axis and is provided with a rotary drive, the upper part of the casing comprising a cover plate having a shell with the extremity of the shell received within the casing below the surface of heat carrier.

In order to provide for better transfer of heat carrier from the pyrolysis zone to the heating zone, and vice versa, radial ribs may be provided on the casing bottom wall.

For intensification of the pyrolysis, a heat source may comprise the active zone of a nuclear reactor arranged in heat carrier.

The invention will now be described with reference to specific embodiments thereof illustrated in the accompanying drawings, in which:

FIG. 1 diagrammatically shows a general view in a longitudinal section of the apparatus for pyrolysis of hydrocarbon starting products according to the invention having an injector with a nozzle for feeding hydrocarbon starting products into heat carrier arranged over the surface of heat carrier;

FIG. 7 shows the apparatus for pyrolysis of hydrocarbon starting products according to the invention in which a means of heat supply to heat carrier comprises the active zone of a nuclear reactor.

The invention contemplates an apparatus and method for pyrolysis of hydrocarbon starting products.

Figure 1:
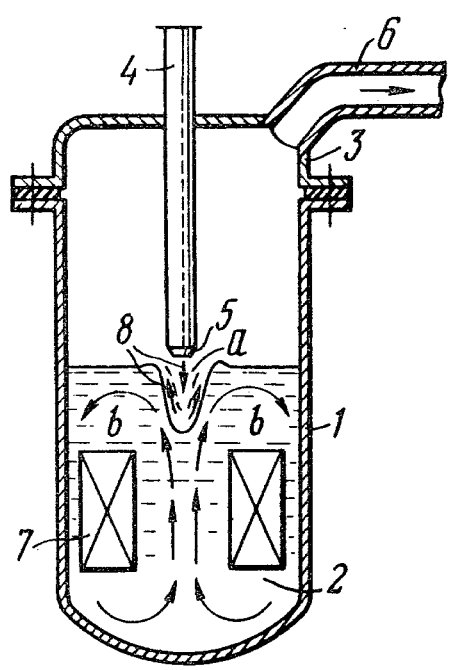

The apparatus shown in FIG. 1 comprises a horizontally split casing 1 for molten heat carrier 2 which in this particular case consists of a melt of heavy metals, such as bismuth. The upper part of the casing 1 which is made in the form of a cover plate 3 accommodates an injector 4 having a nozzle 5 for feeding hydrocarbon starting products into the molten heat carrier 2. The casing 1 has a pipe 6 for removal of pyrolysis products, and there is provided means 7 accommodated within the casing 1, for supplying heat to the heat carrier.

According to the invention, the injector 4 is mounted in the upper part 3 of the casing 1 in such a manner that the outlet section of the nozzle 5 thereof is disposed above the surface of the heat carrier 2 at a distance therefrom which is sufficient for the formation of a hydrodynamic crater 8 in the heat carrier surface under the action of a jet of hydrocarbon starting products flowing from the nozzle 5 as shown by arrow "a." Thus, the nozzle 5 forms a jet supply means for supplying a jet of hydrocarbon starting products to the surface of the heat carrier for creating at the surface of the heat carrier a hydrodynamic crater in which the hydrocarbon starting products travel from the bottom upwardly toward the top of the crater along the crater surface in the form of a thin layer to which heat is supplied from the crater surface.

Figure 2:
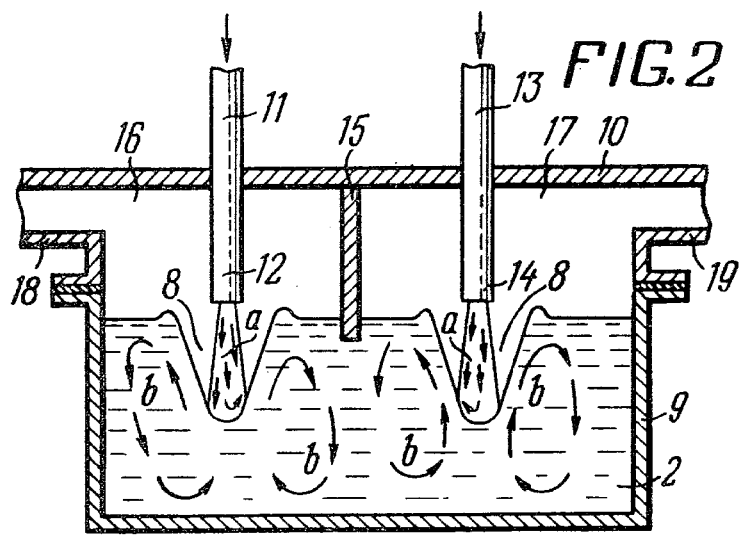
FIG. 2 is a longitudinal section of the apparatus for pyrolysis of hydrocarbon starting products according to the invention having a casing provided with a baffle.

In order that the intensity of heat supply to the heat carrier be equal to the intensity of heat removal for the pyrolysis, the embodiment of the invention shown in FIG. 2 is used. A casing 1 filled with a liquid heat carrier 2 is horizontally split. The upper part, that is a cover plate 10 of the casing 9 accommodates injectors 11 having nozzles 12 for feeding hydrocarbon starting products and injectors 13 having nozzles 14 for feeding gaseous heating agent, such as combustion products at 1900°–2000° C. into the liquid heat carrier 2. The injectors 13 constitute means for supplying heat to the heat carrier 2. To divide the space over the heat carrier for the gaseous phase, there is provided a baffle 15 in the cover plate 10 of the casing 9, the upper and lateral extremities of the baffle being sealingly secured to the cover plate 10, and the lower extremity of the baffle extends slightly below the outlet section of the nozzles 12 and 14 of the injectors 11 and 13 and is submerged in the heat carrier 2.

The baffle 15 divides the space over the heat carrier into two zones 16 and 17 for conducting the pyrolysis and for removal of gaseous heating agent, respectively. For removal of pyrolysis products from the casing 9, there is provided, in the cover plate 10, a pipe 18, and for removal of gaseous heating agent there is provided a pipe 19.

Under the action of the jet flowing from the nozzle to create the craters the heat carrier moves in the direction shown by arrows "b," the transfer of the heat carrier occurring mainly in the vertical direction: from the lower crater region to the top in the zone of the craters 8 and from top down in the peripheral zones.

In addition, the transfer of heat carrier from one zone to the other takes place, hence the heat transfer is effected due to heat conductance of the heat carrier, turbulent pulsations thereof and, to a small extent, due to difference in densities in both zones.

The above-mentioned heat transfer paths do not ensure required intensity of heat transfer from gaseous heating agent to hydrocarbon starting products thus limiting the output of the apparatus.

Figure 3:
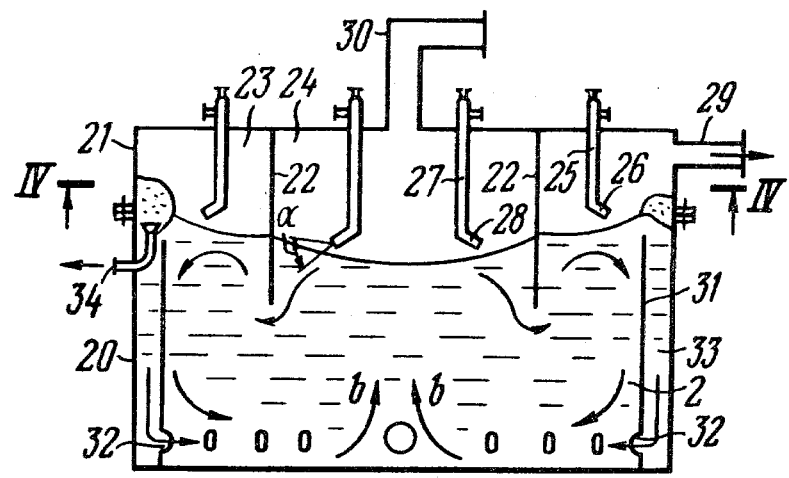
FIG. 3 is a longitudinal section of the apparatus for pyrolysis of hydrocarbon starting products according to the invention having a cylindrical casing and an annular baffle.
Figure 4:
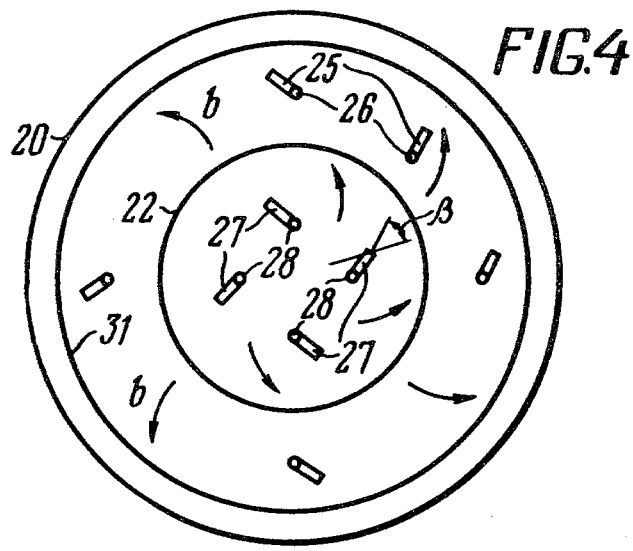
FIG. 4 is a sectional view taken along the line IV—IV in FIG. 3.

Heat transfer is intensified by using the apparatus shown in FIGS. 3 and 4.

In this embodiment, the apparatus comprises a casing 20 and the upper part 21 thereof which are cylindrical in form, and a baffle 22 fixed to and extending from the upper part 21 is annular to divide the space over the heat carrier into two zones 23 and 24 for conducting the pyrolysis and for removal of gaseous heating agent, respectively. The outer zone 23 accommodates injectors 25 with nozzles 26 for feeding hydrocarbon starting products for conducting the pyrolysis, and the inner zone 24 accommodates injectors 27 having nozzles 28 for feeding gaseous heating agent.

The nozzles 26 and 28 of the injectors 25 and 27 are arranged at an acute angle $\alpha$ to the surface of the heat carrier 2, and the outlet sections thereof are located at the surface of the heat carrier 2 and arranged at an acute angle $\beta$ to the radius of the cylindrical casing 20 drawn through the center of the outlet section of the nozzles 26 and 28 of the injectors 25 and 27. The angle $\alpha$ of inclination of the nozzles 26 and 28 to the surface of the heat carrier 2 is from 10° to 40°, and the angle $\beta$ of their inclination to the radius of the casing 20 drawn through the outlet section of the nozzles 26 and 28 is from 15° to 75°.

The upper part 21 of the casing 20 is provided with a pipe 29 for removal of pyrolysis products and a pipe 30 for removal of gaseous heating agent.

The casing 20 has an additional annular baffle 31 mounted between the casing 20 and injectors 25 in such a manner that the upper extremity thereof extends below the surface of the heat carrier 2, and the lower part of the baffle has perforations 32. A space 33 is provided between the wall of the casing 20 and the baffle 31.

The provision of the baffle 31 enables the removal of coke formed during the pyrolysis of hydrocarbon starting products from the apparatus without interrupting its operation.

Due to the flow of the heat carrier 2 in the direction of arrows "b," coke is accumulated at the walls of the casing 20 and removed through a pipe 34 provided for that purpose.

Figure 5:
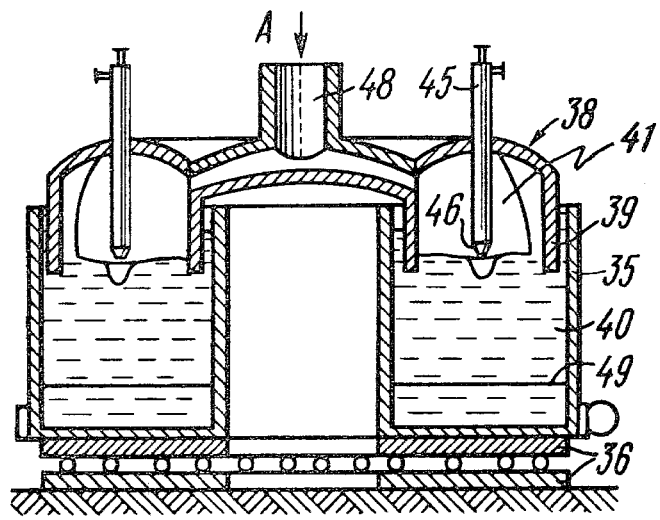
FIG. 5 is a longitudinal section of the apparatus for pyrolysis of hydrocarbon starting products according to the invention having a casing rotatable about the vertical axis.
Figure 6:
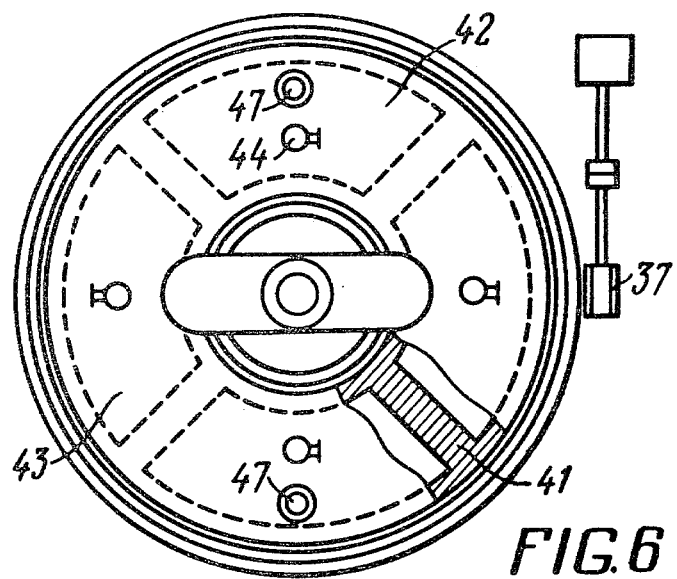
FIG. 6 is a view taken along the arrow A in FIG. 5.

FIGS. 5 and 6 show the embodiment of the apparatus which enables the conduct of pyrolysis in heat carrier having high viscosity ($>1$ P), such as slag melts (in the metal production and the like).

The apparatus comprises a cylindrical casing 35 (FIG. 5) mounted on a movable support 36 which provides for rotation of the casing 35 about a vertical axis. The casing 35 is rotated by a drive 37 (FIG. 6).

The upper part of the casing 35 is made in the form of a cover plate 38 (FIG. 5) having a shell 39 with the extremity of the shell received within the casing 35 below the surface of a heat carrier 40.

The space of the casing 35 over the heat carrier 40 is divided by baffles 41 (FIG. 6) into zones 42 and 43 for conducting the pyrolysis and for heating the heat carrier 40, respectively, and for that purpose the cover plate 38 of the casing 35 supports injectors 44 having nozzles (not shown) for feeding hydrocarbon starting products and injectors 45 having nozzles 46 for feeding gaseous heating agent. There are provided pipes 47 for removal of pyrolysis products and a pipe 48 for removal of gaseous heating agent.

The number of the radial baffles 41 which is mainly determined by the size of the apparatus and its output may be either even or odd. In addition, the baffles may extend not only radially, but also at an angle to the radius of the apparatus.

Radial ribs 9 are provided on the bottom wall of the casing 35 (FIG. 5) to intensify circulation of the heat carrier.

In order to improve the output of the apparatus in terms of starting products, in all embodiments of the apparatus, the upper part of the casing may be provided with a plurality of injectors for feeding hydrocarbon starting products and a plurality of injectors for feeding gaseous heating agent.

A part of pyrolysis products obtained in the pyrolysis zone is generally used for heating the heat carrier in the heating zone of the above-described embodiments of the apparatus. For that reason, such apparatus have lowered yield of pyrolysis products.

For intensification of the pyrolysis process and to improve the yield of products thereof, the active zone of a nuclear reactor may be disposed within the heat carrier directly below the nozzles, the pyrolysis process being intensified due to the radiation of the active zone.

For intensification of the pyrolysis process, the embodiment of the apparatus shown in FIG. 7 is used, wherein a casing 50 partly filled with a heat carrier 51, such as with lead melt, is horizontally split. The upper part 52 of the casing 50 accommodates injectors 53 having nozzles 54 for feeding starting products subjected to the pyrolysis. The active zone 55 of a nuclear reactor is disposed within the heat carrier 51.

A pipe 56 for removal of pyrolysis products is mounted in the upper part 52 of the casing 50.

The apparatus for pyrolysis of hydrocarbon starting products functions in the following manner.

The embodiment illustrated in FIG. 1 is used as an example for explanation of the manner of operation of the apparatus according to the invention and the conduct of the pyrolysis process.

Hydrocarbon starting products are fed to the surface of the liquid heat carrier 2 through the nozzle 5 of the injector 7, the nozzle being located at the heat carrier surface, at a velocity, according to the method of the invention, sufficient for the formation of a hydrodynamic crater 8, the depth of the crater being selected such that the pyrolysis process be conducted intensively. The jet "a" of hydrocarbon starting products moves to the bottom of the crater 8, turns and flow along the arrow "b" upwards in the form of a thin layer (FIG. 1) over the crater surface. It is during the flow of this thin layer over the crater surface which is referred to as backward flow, that heat is supplied. The velocity of the backward flow exceeds the ascent velocity of bubbles by about two orders so that the intensity of heat supply to the starting products materially increases compared to the prior art. The rate of heating of starting products is as high as $10^6°$ C./s, and the time of contact does not exceed 0.1 s. The highest intensity of the process is achieved when the rate of feeding of starting products in the largest section of the crater 8 is $50\, \rho_2 gd/\rho_1$ with the vertical arrangement of the nozzle, wherein $\rho_1$ is density of hydrocarbon starting products at the outlet of the nozzle in kg/m$^3$;

$\rho_2$ is density of the heat carrier in kg/m$^3$;

g is acceleration of gravity, 9.81 m/s$^2$;

d is diameter of the nozzle in m.

Maximum intensity of heating of starting products corresponds to the arrangement of the nozzle at the surface of the heat carrier 2, and with raising thereof the efficiency of the process decreases due to the lowering of the velocity of the starting products jet. When operating with viscous heat carriers, the efficiency of the process is slightly lower with the same velocity compared to the feeding into low-viscosity heat carrier, however, this lowering may be compensated for by increasing the velocity of feeding of starting products, hence by increasing the depth of the crater.

With an increase in the feeding rate, the velocity of the backward flow increases, and the crater surface is enlarged thus explaining the increase of intensity of the process resulting from an increase in the feed rate of starting products, hence in the crater depth. When the starting products are fed in the form of a jet, almost no gas bubbles are formed which would otherwise hamper the pyrolysis.

As mentioned above, hydrocarbon starting products which get to the heat carrier 2 are heated due to intensive transfer of heat from the heat carrier to the starting products.

Thus, pyrolysis products are formed which leave the crater 8 and emerge into the space over the heat carrier 2 to be removed therefrom through the pipe 6.

Due to the interaction of the jet of hydrocarbon starting products and the heat carrier, circulation in the vertical plane as shown by arrows "a" and "b," respectively, in FIG. 2 develops in the heat carrier. Heat is supplied to the heat carrier from means 7 for supplying heat. In this apparatus, the intensity of heat supply to the heat carrier from means 7 may prove insufficient due to insufficient heat transfer on the surface thereof.

For intensification of the heat supply, the embodiment shown in FIG. 2 is used, in which gaseous heating agent is fed also in the form of a jet to the surface of the heat carrier 2 through the nozzle 14 of the injector 13.

The intensity of heat transfer from gaseous heating agent to the heat carrier 2 is equal to the intensity of heat removal for pyrolysis. The baffle 15 ensures the sealed division of the space over the heat carrier into two zones, one zone 16 containing pyrolysis products and the other zone 17 containing gaseous heating agent.

Pyrolysis products are removed from the apparatus through the pipe 18, and the gaseous heating agent is removed through the pipe 19. As a result of interaction of jets of hydrocarbon starting products and gaseous heating agent and the heat carrier, circulatory motion develops in the heat carrier in the vertical plane as shown by arrows "b" in FIG. 2.

The flow of heat carrier 2 between the parts 16 and 17 of the casing 9 develops due to turbulent pulsations and difference in densities of the heat carrier in both zones 16 and 17.

The transfer of heat between the zones of the apparatus occurs as a result of flow of the heat carrier between the above-mentioned zones 16 and 17, as well as due to heat conductance.

All the above-mentioned heat transfer paths do not provide for sufficiently intensive transfer of heat from gaseous heating agent to hydrocarbon starting products so that the output of the apparatus shown in FIG. 2 is limited.

Heat transfer between the pyrolysis and heating zones is intensified to a larger extent in the embodiment of the apparatus shown in FIGS. 3 and 4.

With the illustrated arrangement of the nozzles 26 and 28 of the injectors 25 and 27, the outflowing jets of starting products and gaseous heating agent, respectively, result in the development of circular and radial motions (from the center to the periphery of the casing in the upper layers of the heat carrier 2 and radial motion from the periphery to the center in the lower layers of the heat carrier). Due to the centrifugal action, as well as due to the radial flow, an intensive overflow of the heat carrier 2 from the heating zone 24 located at the center to the zone 23 of pyrolysis of hydrocarbon starting products is ensured.

The annular baffle 22 and the cylindrical casing 20 provide for minimum resistance to the circular motion of the heat carrier 2.

During operation of the apparatus, some quantity of coke is formed which accumulates on the surface of the heat carrier 2 and hampers the operation, if continuous removal thereof is not effected.

The baffle 31 is provided for cleaning the apparatus from coke without interrupting the operation. Coke is thrown to the periphery of the casing 20 due to the action of jets of starting products and motion of the heat carrier, and at the periphery, the coke, together with a part of the heat carrier 2, flows over the upper extremity of the baffle 31. The heat carrier 2 separated from coke descends within the space 33 between the casing 20 and the additional baffles 31 and leaves it through the perforations 32, and the coke accumulates in the space 33 wherefrom it may be removed through the pipe 34 without interrupting the operation of the apparatus.

Optimum angle of inclination of the nozzles to the surface of the heat carrier ranges from 10° to 40° since with greater angles of inclination, the fraction of kinetic energy of jets flowing from the nozzles of injectors transferred to the liquid decreases, that is circulation is impaired, and with smaller angles, the heat exchange is impaired due to a material reduction of crater depth. Optimum angle of inclination of the nozzles axes to the radius of the casing ranges from 15° to 75° since the radial and tangential components determining the transfer of the heat carrier are sufficiently high within this range. With smaller angles, the tangential component is too low, and with greater angles, the radial component is too low.

When operating with viscous heat carriers, the above-described embodiment of the apparatus does not provide for sufficient heat transfer between the pyrolysis and heating zones due to the fact that the energy of jets flowing from the nozzles 26 and 28 is not enough for ensuring sufficiently intensive circulation of the heat carrier 2. The embodiment of the apparatus shown in FIGS. 5 and 6 solves this problem.

In this case, rotation of the casing 35 provides for rotary motion of the heat carrier 40 due to viscosity so that the heat carrier is transferred from the pyrolysis zones 42 to the heating zones 43 and again to the pyrolysis zones 42 thus effecting the heat transfer from one zone to another. Radial ribs 49 are provided on the bottom wall of the casing 35 to intensify rotation of the heat carrier.

The embodiment shown in FIG. 7 is used for improvement of the yield of low-molecular hydrocarbons, including olefins, the feeding of starting products being effected similarly to the above-described embodiments.

It should be noted that during the passage of starting products through the crater 8 and in the space over the heat carrier 51, the starting products are not only heated to the reaction temperature, but also subjected to the action of intensive radiation of a nuclear reactor.

The pyrolysis in the flow of starting products occurs more intensively under the action of radiation due to the appearance of larger number of radicals of the $CH_3$ or $H$ type in the reaction mixture.

Thus, pyrolysis products with lower molecular weight may be obtained with an increased yield of olefins.

Circulation of the heat carrier 51 shown by arrows "b" in FIG. 7 contributes to intensification of heat supply from the active zone of the reactor of the heat carrier and to the lowering of temperature of structural materials of which it is made.

The invention enables simplification of construction of the apparatus for pyrolysis and operation thereof, provides for reduction of metal consumption in the manufacture of the apparatus and ensures reduction of capital investments and operation expenses in the petrochemical industry.

The process of pyrolysis according to the invention may be readily automated. This provides for maintenance of optimum performance of the pyrolysis to ensure maximum yield of valuable chemical products.

As is apparent from the above description, the method of the invention includes such features as introducing the hydrocarbon starting product downwardly towards the heat carrier at the region of the surface thereof in the form of a jet at a velocity sufficient to form at the surface of the heat carrier a hydrodynamic crater at the surface of which the starting products flow in the form of a thin layer from the bottom towards the top of the crater to receive heat from the heat carrier, a gaseous heating agent being introduced in the same way, as shown in FIG. 2, while according to embodiments as shown in FIGS. 2–6, the space above the heat carrier is divided by one or more baffles extending only slightly below the surface of the heat carrier into pyrolysis and heating zones with the heat carrier being free to travel between these zones, the embodiments of FIGS. 3–6 including the additional feature of setting the heat carrier into rotart motion about a vertical axis, by way of the jets themselves according to FIGS. 3 and 4 and by way of rotating the casing according to FIGS. 5 and 6, so as to improve the operation in this way. Of course, the embodiment of FIGS. 3 and 4 includes the additional feature of removing products from the surface of the heat carrier at the region of the outer periphery of this surface by way of the outer baffle 31, which is formed with perforations adjacent its lower edge, and the discharge pipe 34.

We claim:

1. In a method for carrying out pyrolysis of hydrocarbon starting products utilizing a casing having a substantially cylindrical side wall and a liquid heat carrier disposed therein said liquid heat carrier being at a predetermined level in said casing and defining a space above the surface of said liquid heat carrier, a substantially cylindrical baffle located within said casing substantially coaxially with respect to said cylindrical wall and dividing said space into a heating zone and a pyrolysis zone, said baffle extending a small distance below the surface of said heat carrier, the insulation comprising the steps of:

directing a jet of gaseous heating agent onto the surface of the heat carrier in the heating zone;
   directing a jet of hydrocarbon starting products onto the surface of the heat carrier in the pyrolysis zone so than an intensive heat transfer occurs from the heat carrier to the hydrocarbon starting products which contact the surface of the heat carrier whereby pyrolysis products are formed; and
   removing the pyrolysis products from said casing.

2. A method as defined in claim 1 wherein said jet of gaseous heating agent and said jet of hydrocarbon starting products are directed onto the surface of the heat carrier to form an acute angle of inclination with the surface of the heat carrier and wherein the outlet sections of said jet of heating agent and said jet of hydrocarbon starting products are located at the surface of the heat carrier and arranged at acute angles with respect to the radius of said casing drawn through the center of the outlet section of said nozzles.

3. A method as defined in claim 2 further including the step of providing an additional substantially cylindrical baffle coaxial with the casing in a region adjacent to the side wall of the casing having an upper edge located below the surface of the heat carrier and a lower edge region having apertures formed therein.

* * * * *